(12) United States Patent
Park et al.

(10) Patent No.: US 7,115,136 B2
(45) Date of Patent: Oct. 3, 2006

(54) ANASTOMOTIC DEVICE

(75) Inventors: Adrian Edward Park, Nicholasville, KY (US); Charles Francis Knapp, Georgetown, KY (US)

(73) Assignee: ParK Medical LLC, Nicholasville, KY (US)

( * ) Notice: Subject to any disclaimer, the term of this patent is extended or adjusted under 35 U.S.C. 154(b) by 664 days.

(21) Appl. No.: 10/288,577

(22) Filed: Nov. 6, 2002

(65) Prior Publication Data

US 2003/0120292 A1   Jun. 26, 2003

Related U.S. Application Data

(63) Continuation-in-part of application No. 10/175,159, filed on Jun. 20, 2002.

(60) Provisional application No. 60/299,618, filed on Jun. 20, 2001.

(51) Int. Cl.
*A61B 17/11*    (2006.01)
*A61M 29/00*    (2006.01)

(52) U.S. Cl. .................. 606/155; 606/153; 606/108; 128/898

(58) Field of Classification Search .......... 606/108, 606/139, 142, 153, 155, 184, 185; 623/1.11
See application file for complete search history.

(56) References Cited

U.S. PATENT DOCUMENTS

| | | | |
|---|---|---|---|
| 4,655,771 A | 4/1987 | Wallsten | 623/1 |
| 4,665,906 A | 5/1987 | Jervis | 128/92 YN |
| 4,733,665 A | 3/1988 | Palmaz | 128/343 |
| 5,067,957 A | 11/1991 | Jervis | 606/108 |
| 5,197,978 A | 3/1993 | Hess | 623/1 |
| 5,376,376 A | 12/1994 | Li | 424/443 |
| 5,466,242 A | 11/1995 | Mori | 606/198 |
| 5,540,712 A | 7/1996 | Kleshinski et al. | 606/198 |
| 5,575,818 A | 11/1996 | Pinchuk | 623/1 |
| 5,601,593 A | 2/1997 | Freitag | 606/198 |
| 5,676,670 A | 10/1997 | Kim | 606/108 |
| 5,720,776 A | 2/1998 | Chuter et al. | 623/1 |
| 5,725,552 A | 3/1998 | Kotula et al. | 606/213 |
| 5,741,333 A | 4/1998 | Frid | 623/12 |
| 5,797,920 A | 8/1998 | Kim | 606/108 |

(Continued)

FOREIGN PATENT DOCUMENTS

WO    WO 03/003926    1/2003

OTHER PUBLICATIONS

Cogdon, C. et al, "Numerical Analysis of An Anastomotic Device," *Computer Methods in Biomechanics and Biomedical Engineering*, 2002 vol. 5(1), pp. 53-65.

*Primary Examiner*—Julian W. Woo
*Assistant Examiner*—Sarah Webb
(74) *Attorney, Agent, or Firm*—Steptoe & Johnson LLP

(57) ABSTRACT

The present invention is directed to gastrointestinal or enteric (including biliary) anastomosis and the like. The anastomotic device of the invention is a three dimensional woven tube of wire. The outer loops or ends of the tube fold or loop back on deployment in a manner which holds the luminal interface of the anastomotic site into apposition at the deployment site. The woven tube is deployed using a protective sleeve and nose assembly. Adjustment of the wire diameter and/or material properties of the wire can cause the anastomotic device to remain in place permanently or, for example, in the case of the intestine to slough through the two apposing walls of the lumen resulting in the device safely passing through the intestine leaving a naturally healed, properly functioning anastomosis.

11 Claims, 7 Drawing Sheets

U.S. PATENT DOCUMENTS

| | | | |
|---|---|---|---|
| 5,876,434 A | 3/1999 | Flomenblit et al. | 623/1 |
| 5,876,445 A | 3/1999 | Andersen et al. | 623/11 |
| 5,938,697 A | 8/1999 | Killion et al. | 623/1 |
| 6,007,544 A | 12/1999 | Kim | 606/108 |
| 6,007,574 A | 12/1999 | Pulnev et al. | 623/1 |
| 6,077,281 A | 6/2000 | Das | 606/151 |
| 6,077,291 A | 6/2000 | Das | 606/213 |
| 6,113,612 A | 9/2000 | Swanson et al. | 606/153 |
| 6,123,715 A | 9/2000 | Amplatz | 606/200 |
| 6,152,937 A | 11/2000 | Peterson et al. | 606/153 |
| 6,165,185 A | 12/2000 | Shennib et al. | 606/155 |
| 6,193,734 B1 | 2/2001 | Bolduc et al. | 606/153 |
| 6,206,912 B1 * | 3/2001 | Goldsteen et al. | 606/108 |
| 6,206,913 B1 | 3/2001 | Yencho et al. | 623/1.3 |
| 6,231,587 B1 | 5/2001 | Makower | 606/198 |
| 6,309,415 B1 | 10/2001 | Pulnev et al. | 623/1.22 |
| 6,616,675 B1 * | 9/2003 | Evard et al. | 606/155 |

* cited by examiner

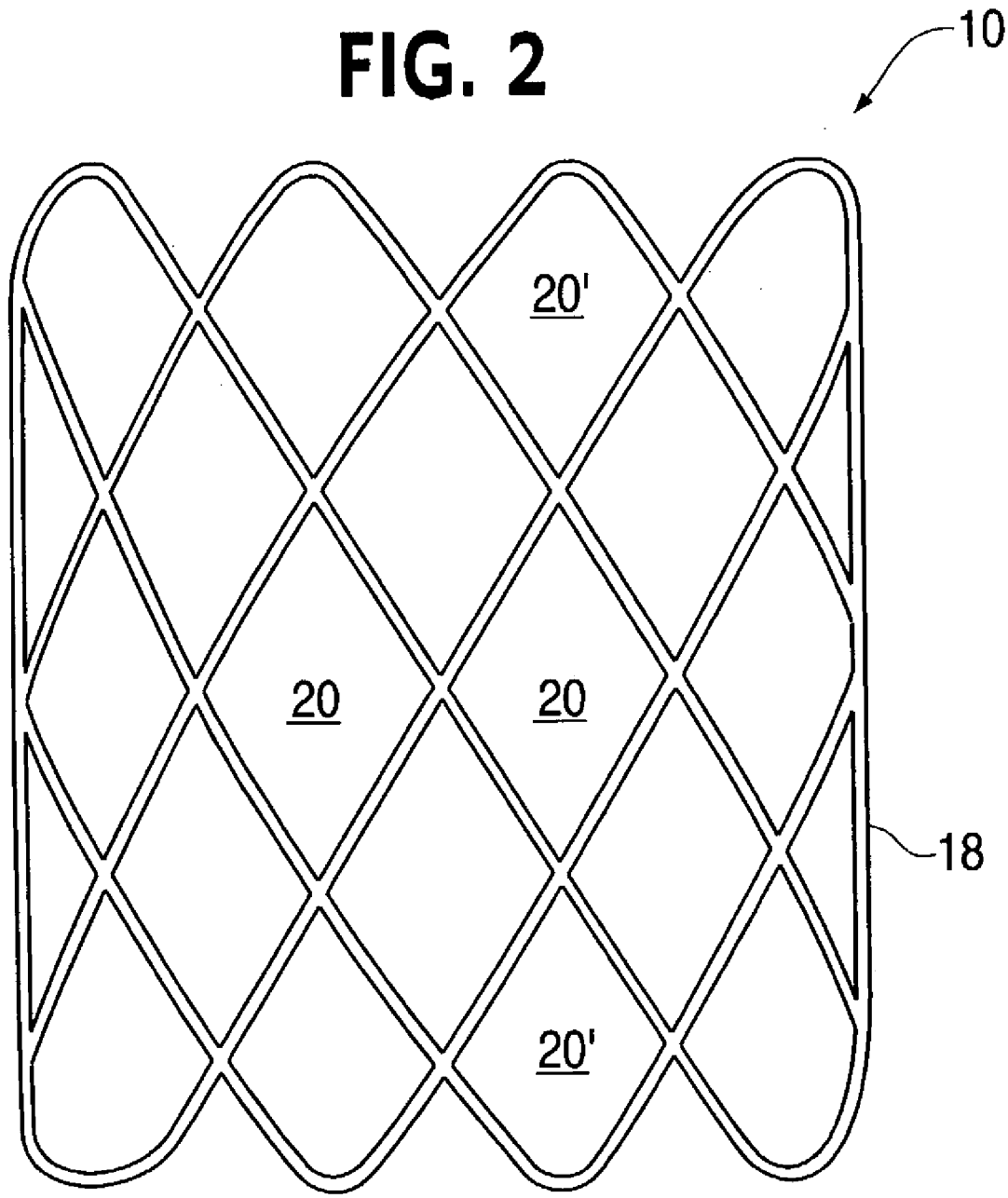

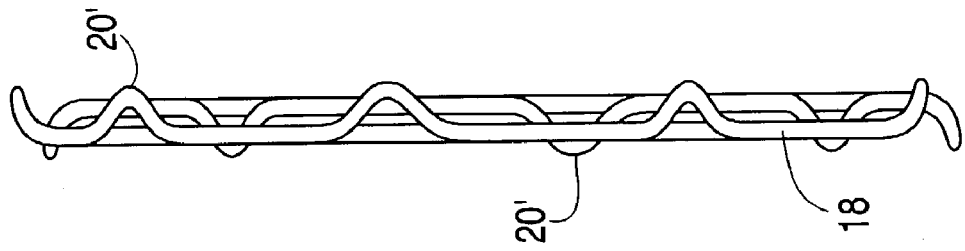
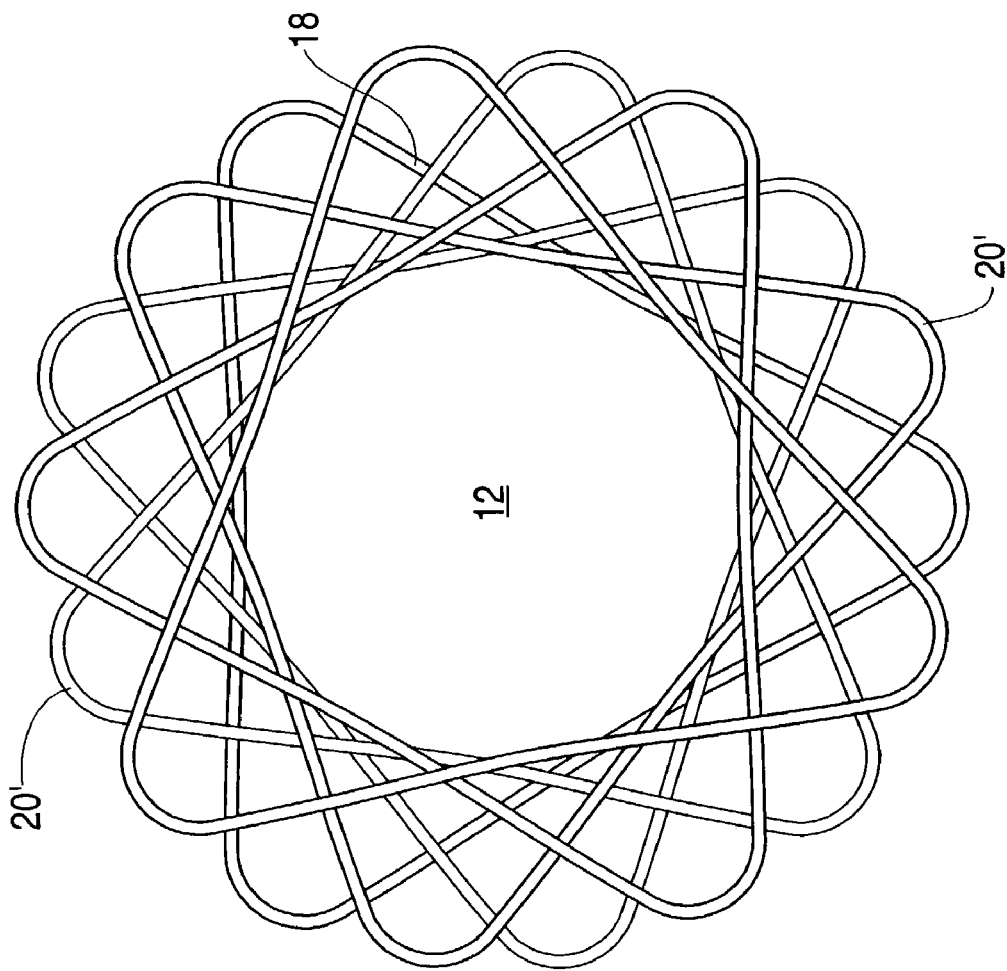

ANASTOMOTIC DEVICE

The present application is a continuation-in-part of application Ser. No. 10/175,159, filed Jun. 20, 2002, which claims the benefit of provisional application Ser. No. 60/299,618, filed Jun. 20, 2001.

BACKGROUND OF THE INVENTION

1. Field of the Invention

The present invention is directed to gastrointestinal and enteric (including biliary) anastomoses and the like. The woven tube of wire of the invention is a three dimensional structure wherein the outer loops or ends of the woven tube fold or loop back in a manner which holds the luminal interface of the anastomotic site into apposition at the deployment site. The woven tube, depending on material utilized, could either hold the lumen walls in apposition as a permanent fixture eventually incased by scar tissue or remain in place temporarily until sufficient healing occurs between the walls of the intestine, for example, at which time the anastomotic device sloughs from the intestine and is safely passed, leaving a properly functioning anastomosis.

2. Description of the Related Art

Surgical procedures often require the joining (anastamosis) of two vessels or hollow vicera. For example, a permanent anastomosis between the stomach and intestine may be required in the performance of gastric bypass surgery for the morbidly obese as well as to alleviate blockage in the common bile duct by draining bile from the duct to the small intestine during surgery for pancreatic cancer. Surgical anastomosis generally involves manual suturing of the two structures. This process can be technically demanding and time consuming. This complex surgical procedure is even more challenging during minimally invasive surgery (MIS) where the surgeon is required to use instruments that are poorly designed for this task.

SUMMARY OF THE INVENTION

The present invention is directed to a woven tube of wire for use in an automated anastomotic delivery device for surgery with special emphasis on MIS. The primary component is the woven tube of wire which deforms to make an anastomotic device when inserted into the walls of two adjacent vessels or lumens. The use of such a device for joining (anastomosing) two gastrointestinal or enteric (including biliary) vessels or lumens or the like is new.

The anastomotic delivery device is designed with a protective sleeve to encapsulate the woven tube and a removable nose assembly to permit the woven tube to be inserted into the protective sleeve via a loading apparatus. The woven tube is pulled longitudinally causing the tube to become longer and very small in diameter and is installed into a loading apparatus. The loading apparatus consists of a sheath and attached alignment cylinder and a plunger. The loading apparatus is designed to fit over the end of the protective sleeve of the delivery device to permit ease of reloading for multiple deployments. To load the woven tube into the delivery device, the nose assembly is removed from the delivery device and the loading apparatus is fit over the protective sleeve. The plunger of the loading apparatus moves the woven tube into the protective sleeve of the delivery device. After the woven tube is installed in the delivery device, the nose assembly is placed over the protective sleeve to encapsulate the woven tube between the nose assembly and a ram.

The loaded delivery device is inserted into the appropriate vessel or lumen either manually or with the aid of a previously positioned guide wire. A small sharp knife, initially retracted in the center of the nose assembly, is exposed at the tip (such as by pushing on a button in the handle) in order to assist the surgeon when passing the delivery device through the walls of the vessels or lumens. The nose assembly and protective sleeve penetrate both walls and are properly positioned with the tissues against an alignment sleeve on the delivery device which serves as a tissue stop at this point in the procedure. The woven tube is then partially deployed from the protective sleeve by movement of the ram, while simultaneously the alignment sleeve positions the tissues onto the woven tube. Once the tissues are in proper position, the woven tube is completely deployed from the protective sleeve while simultaneously alignment struts or an alignment buttress mechanism insures proper positioning of the tissues during closure of the woven tube. Closure of the woven tube is accomplished by forces resulting from shape memory or spring metal properties of the woven tube and/or by compression of the woven tube by the delivery device which can supply forces against the petals of the woven tube to insure a properly functioning anastomosis.

The mechanical force of the woven tube against the lumen walls which creates the anastomosis is dependent on the material utilized in the manufacturing of the woven tube. With a woven tube created from a thermal shape memory alloy such as nitinol, heat from the body causes the woven tube to contract longitudinally to produce the anastomosis. With a woven tube created from spring material, the supplied force to bold the lumen walls in apposition occurs when the material springs back to initial form. With a woven tube manufactured from compressible material, the final shape of the woven tube is formed mechanically by the compression action of the delivery device. With either approach, sufficient force is applied to the wall tissues such that the hole between the two lumens is enlarged (for drainage) and leakage outside the two lumens does not occur. When used in the intestine, for example, the mechanical force from the wire mesh of the anastomotic device to keep the lumen walls held in apposition can be varied dependent on wire diameter and/or material properties resulting in the anastomotic device being either a permanent fixture or remaining temporarily in place until sufficient healing occurs between the intestine at which time the anastomotic device sloughs from the intestine and is safely passed leaving a properly functioning anastomosis.

Additional objects, advantages and other novel features of the invention will be set forth in part in the description that follows and in part will become apparent to those skilled in the art upon examination of the foregoing or may be learned with the practice of the invention.

BRIEF DESCRIPTION OF THE DRAWINGS

FIG. 2 is a side view of the woven tube pulled longitudinally prior to being placed into the protective sleeve of the delivery device.

FIG. 3A is a front view of the woven tube similar to FIG. 1 with the walls of the lumens being omitted.

FIG. 3B is a side view of the woven tube of FIG. 3A.

DESCRIPTION OF THE PREFERRED EMBODIMENTS

Figure 1:
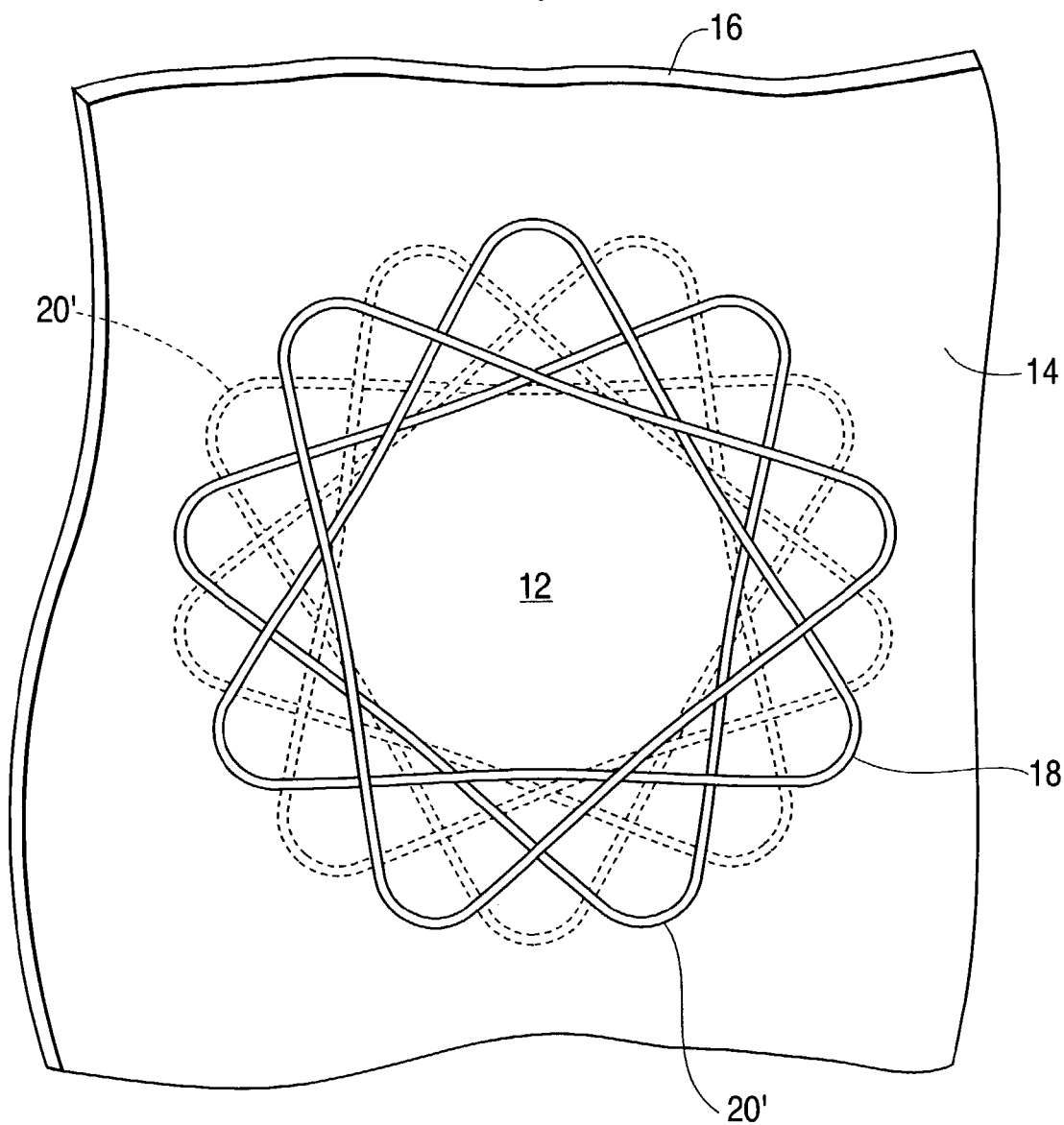
FIG. 1 is a front view of the woven tube of wire in its deployed form in which the outer loops or ends of the woven tube have deformed and everted to form petals which hold the walls of the lumens into apposition, the front and back petals of the deployed anastomotic device being shown as dark black and light gray lines, respectively.

The tube 10 has an overlapping woven design. The woven tube is designed to produce a round opening 12 between two layers of tissue 14, 16 and to hold the layers of tissue together for a watertight seal. The deployed anastomic device is essentially a woven tube 10 of wire 18 that is axially compressed as shown in FIG. 1.

The woven tube 10 is defined by the wire diameter, number of circumferential and longitudinal openings or diamonds 20, the tube length and the center diameter. The openings or diamonds 20' at the longitudinal ends of the elongated woven tube are referred to as petals when the device is in the deployed shape (see FIG. 1).

In use, the woven tube 10 is forced into an elongated form (with much smaller diameter than that shown in FIG. 2), placed through openings between the wall tissues of two lumens and allowed or forced to return to the flattened shape of FIG. 1. In the process, the tissues of both lumen walls are compressed between the petals of the flattened tube (see FIG. 1) with the center diameter 12 of the flattened tube forming an opening between the lumens.

The woven tube 10 can be applied, for example, through the common bile duct, and pushed through so that it connects the duct to the jejunum. After the connection has been made, the tube can be caused to deform and evert so that the ends spread out like the petals of a flower and form a connection between the two ducts. The woven tube 10, depending on wire diameter and/or material properties utilized, could either hold the lumen walls in apposition as a permanent fixture eventually incased by scar tissue or remain in place temporarily until sufficient healing occurs between the tissue layers at which time the anastomotic device sloughs from the intestine and is safely passed leaving a properly functioning anastomosis. As a general rule, a larger wire diameter will result in greater mechanical force and a tendency for the anastomotic device to slough from the intestine. The material properties can be varied, for example, by the selection of the annealing temperature of the wire metal to facilitate either a permanent fixture or a temporary fixture.

The woven tube 10 may be made out of a shape memory metal. A shape memory metal is an alloy that changes its plasticity as heat is applied, allowing it to change shape. If a shape memory metal is annealed in a desired form (in a longitudinally compressed form), after it is reshaped (in a cylindrical tube form) it will return to its annealed shape (flattened form) if it is reheated at a significantly lower temperature. The very special property of thermal memory is especially helpful in the design of a low profile and flexible delivery system. The preferred shape memory metal is a titanium-nickel alloy, most preferably a nearly equiatomic alloy of titanium and nickel called nitinol. Specific nitinol alloys, which also have superelastic properties, can reshape at body temperature.

The woven tube 10 may also be made out of a spring material. In this case, the supplied force to hold the lumen walls in apposition occurs when the wire material springs back to initial form.

As a further alternative, the woven tube 10 may be manufactured from compressible wire material. In this case, the final shape of the woven tube is formed mechanically by the compression action of the delivery device.

The anastomotic delivery device 22 is designed with a protective sleeve 26 to encapsulate the woven tube 10 and a removable nose assembly 30 to permit the woven tube 10 to be inserted into the protective sleeve 26 via a loading mechanism 42. The woven tube 10 is pulled longitudinally causing the tube to become longer and very small in diameter and is installed into the loading mechanism 42. The loading mechanism 42 consists of a sheath 48 and plunger 50 and includes an alignment cylinder 52 designed to fit over the end of the protective sleeve 26 of the delivery device 22 to permit ease of reloading for multiple deployments. To load the woven tube 10 into the delivery device 22, the nose assembly 30 is removed from the delivery device 22 and the loading mechanism 42 is fit over the protective sleeve 26. The plunger 50 of the loading mechanism 42 moves the woven tube 10 into the protective sleeve 26 of the delivery device 22. After the woven tube 10 is installed in the delivery device 22, the nose assembly 30 is reinstalled to encapsulate the woven tube 10 between the nose assembly 30 and a cylindrical ram 36.

The nose assembly 30 includes a first hollow shaft 54 which fits in the opening of cylindrical ram 36. The nose assembly further includes a second hollow shaft 56 which is positioned in the hollow opening of the first hollow shaft 54 in telescoping fashion. The nose assembly has a streamlined nose 58 and a rounded base 60. The proximal end of the first hollow shaft 54 is attached to the rounded base 60. The proximal end of the second hollow shaft 56 is attached to the streamlined nose 58. The nose assembly also has a hollow rubber or plastic cylinder 62 between the streamlined nose 58 and the rounded base 60. A first stop 64 is attached to the distal end of the streamlined nose 58 and a second stop 66 is attached to the proximal end of the rounded base 60.

In use in a side-to-side intestinal anastomosis, for example, the delivery device 22 is inserted into the body cavity either manually or, as shown, with the aid of a previously positioned guide wire 38 (which passes through second hollow shaft 56 and an opening in knife blade 34) through a trochar or tube (not shown) and the streamlined nose 58 of the delivery device 22 is positioned at a predetermined puncture site in a first intestinal segment 28 either proximal or distal to the desired anastomotic site and the delivery device 22 is advanced intraluminally to the anastomotic site.

Figure 4A:
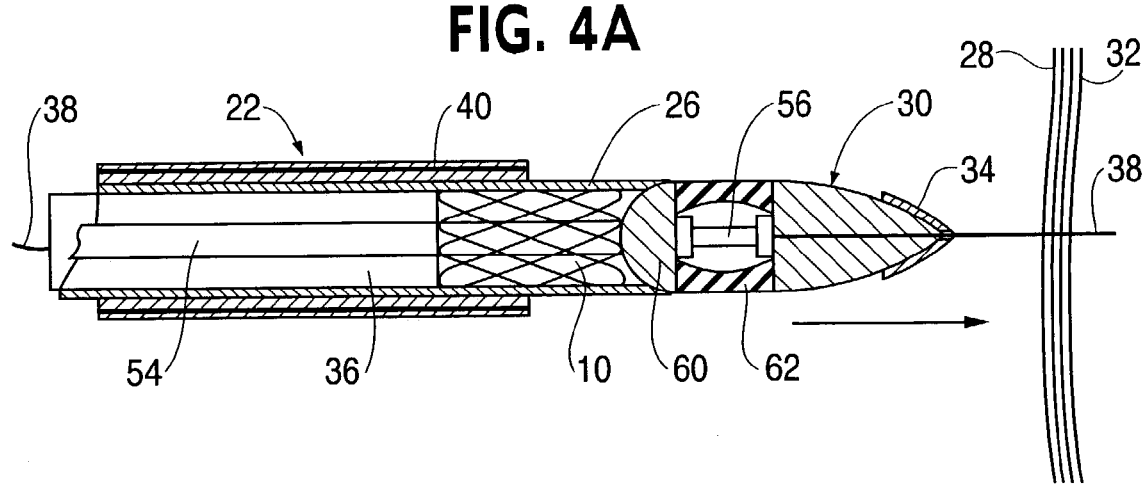
FIG. 4A is a cross-sectional view of the delivery device inserted into a body cavity either manually or, as shown, assisted by a previously positioned guide wire to a predetermined anastomotic site having the woven tube loaded inside the protective sleeve between the ram and the nose assembly with the knife deployed in preparation to puncture the lumen walls.
Figure 4B:
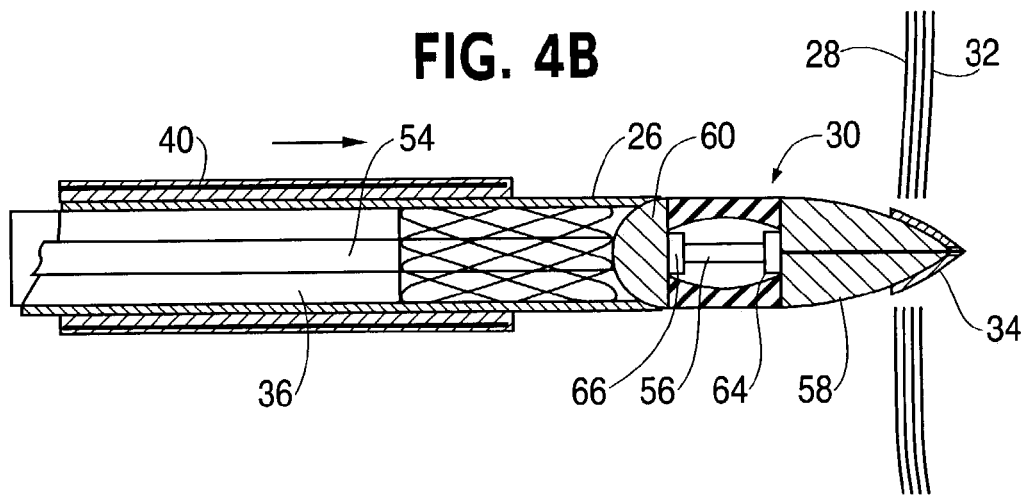
FIG. 4B shows the end of the delivery device piercing the lumen walls using the retractable knife.
Figure 4C:
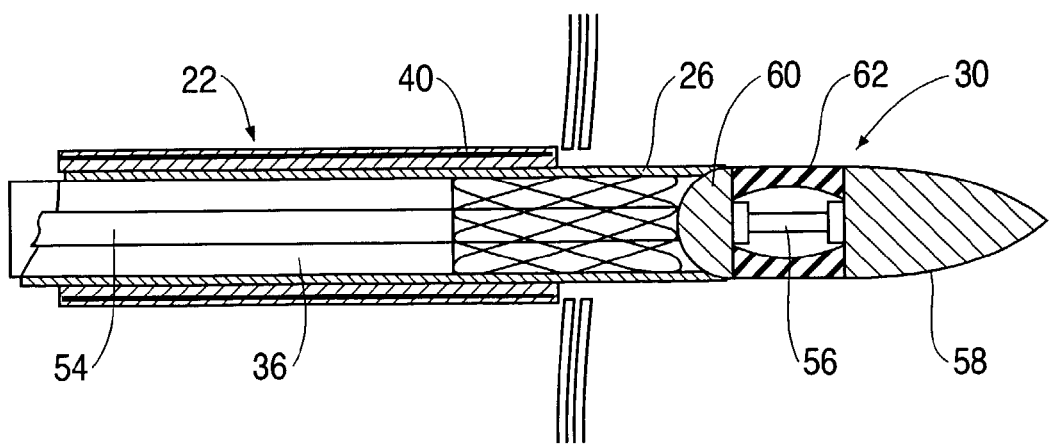
FIG. 4C shows the end of the delivery device passed through the puncture created by the knife (now retracted) with the lumen walls over the protective sleeve and against the alignment sleeve.

The second intestinal segment 32 is brought into close apposition to the first segment at the anastomotic site and a knife blade 34, initially retracted in the center of the streamlined nose 58, is used to pierce through the wall of the first segment 28 and the wall of the second segment 32 and into the lumen of the second segment positioning the tissue against the alignment sleeve 40 as shown in FIG. 4C. The woven tube 10 is deployed as shown in the sequences of FIGS. 4D, 4E, 4F, 4G and 4H at the juncture of the apposing holes created by the knife blade 34 and assumes the petal configuration at the site to hold the two pieces of intestine in apposition. The woven tube 10 deployed through the two layers of intestine is shown in FIGS. 4G, 4H and 4I. The opposed petals 20 on opposite sides of the two layers of intestine 28, 32 are preferably interdigitated as shown in FIGS. 1, 3A and 3B.

Figure 4D:
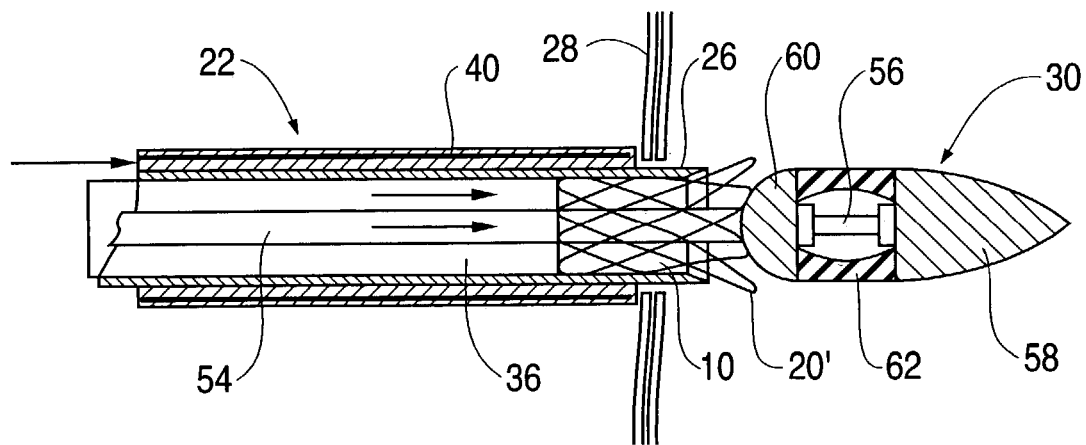
FIG. 4D shows the partial deployment of the woven tube from the end of the protective sleeve via the movement of the ram, nose assembly and alignment sleeve.
Figure 4E:
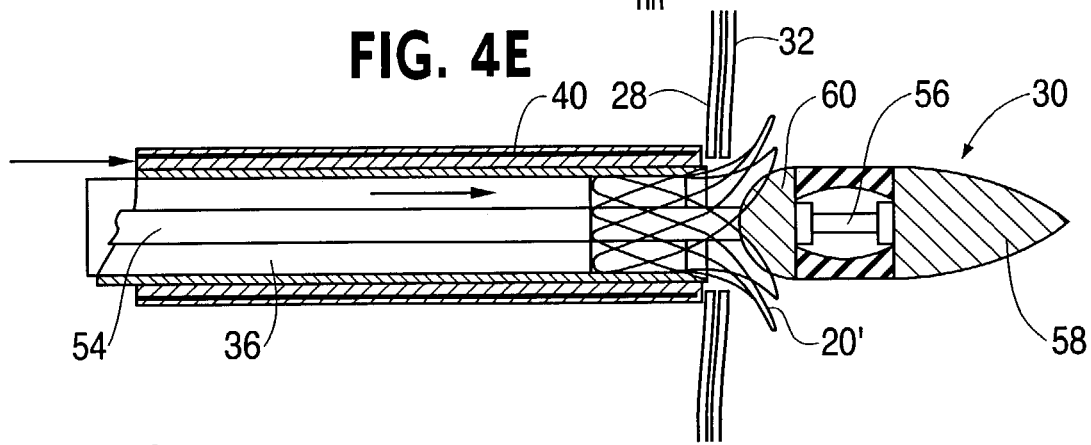
FIG. 4E shows the continued deployment of the woven tube via the further movement of the ram which promotes the expansion of the woven tube. Simultaneously, the alignment sleeve pushes the tissues from the protective sleeve toward the center of the woven tube before full deployment of the woven tube.
Figure 4J:
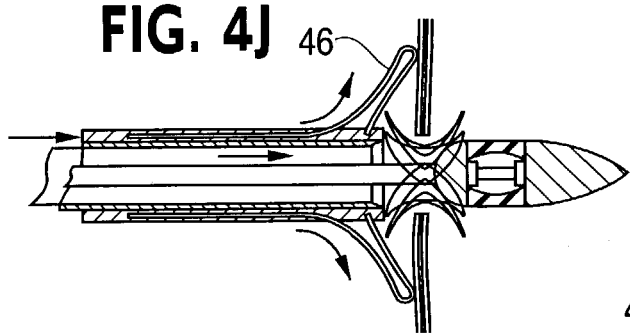
FIG. 4J shows the same action of FIG. 4F with the final push of the woven tube from the protective sleeve via the movement of the ram and the nose assembly except that an alignment buttress mechanism is used instead of the alignment struts. Simultaneously with the movement of the ram and nose assembly, the alignment buttress mechanism is deployed over the alignment sleeve insuring proper placement of the tissue during closure of the woven tube.
Figure 4F:
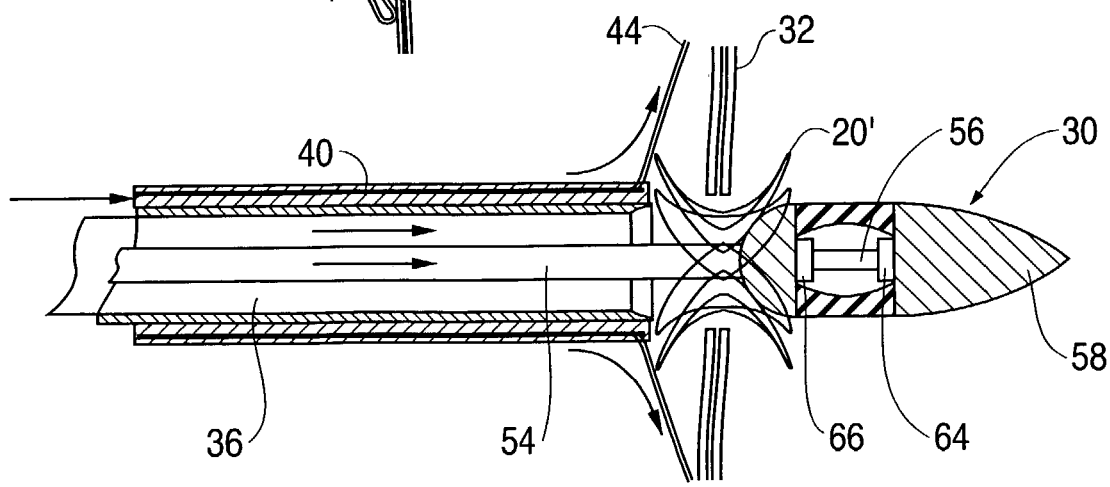
FIG. 4F shows the final push of the woven tube from the protective sleeve via the movement of the ram and nose assembly. Simultaneously, the alignment struts are deployed from the alignment sleeve at a predetermined angle assisting proper placement of the tissues during closure of the woven tube.
Figure 4G:
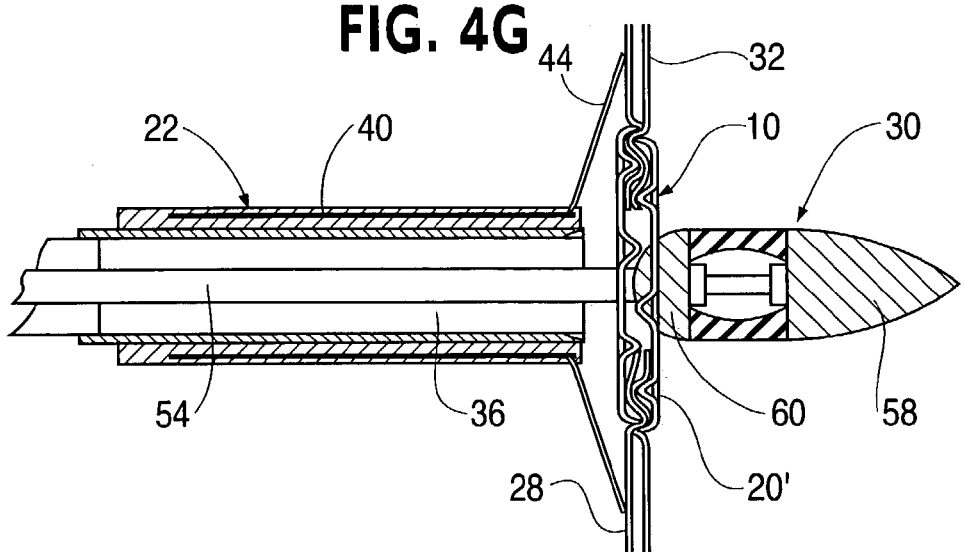
FIG. 4G shows the delivery device inside the woven tube deployed about the lumen.
Figure 4H:
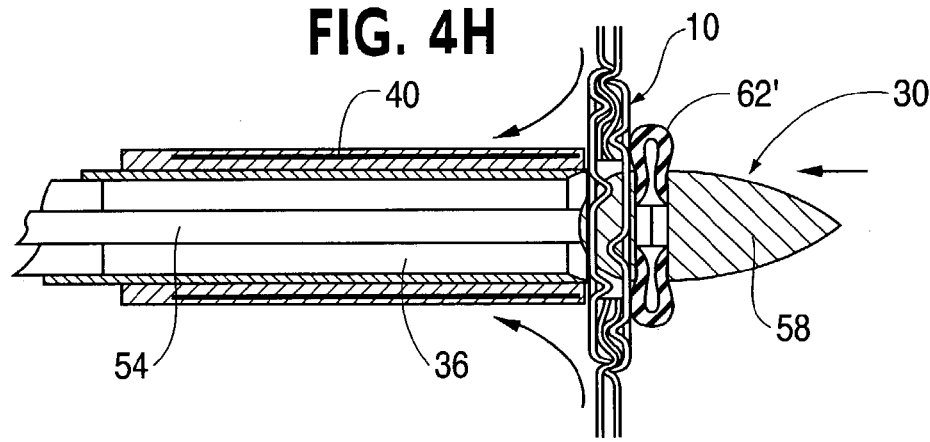
FIG. 4H shows the retraction of the alignment struts, the alignment sleeve positioned against one side of the deployed woven tube, and the nose assembly contracted to form the compressed buttress positioned against the opposite side of the deployed woven tube to insure complete closure.
Figure 4I:
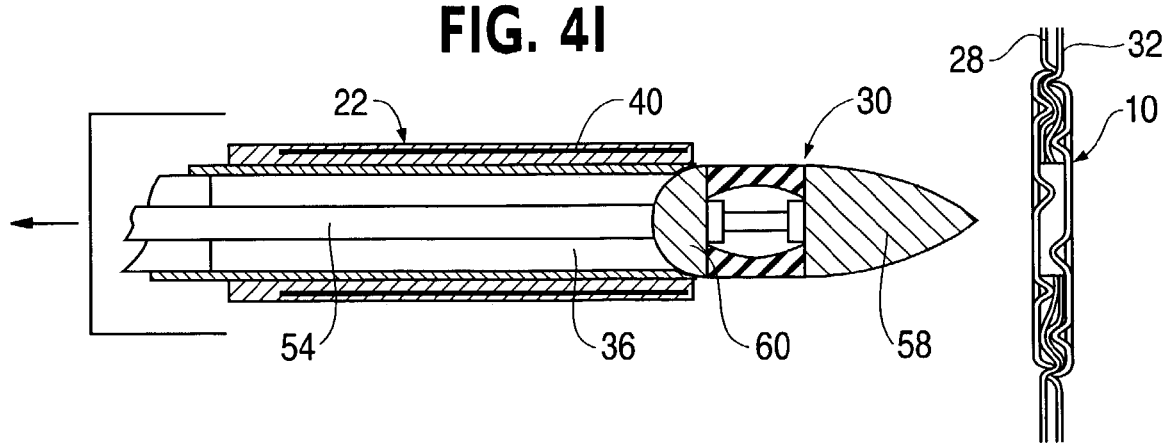
FIG. 4I shows the nose assembly extended to retract the compressed buttress and the delivery device removed from the center of the deployed woven tube.
Figure 5A:
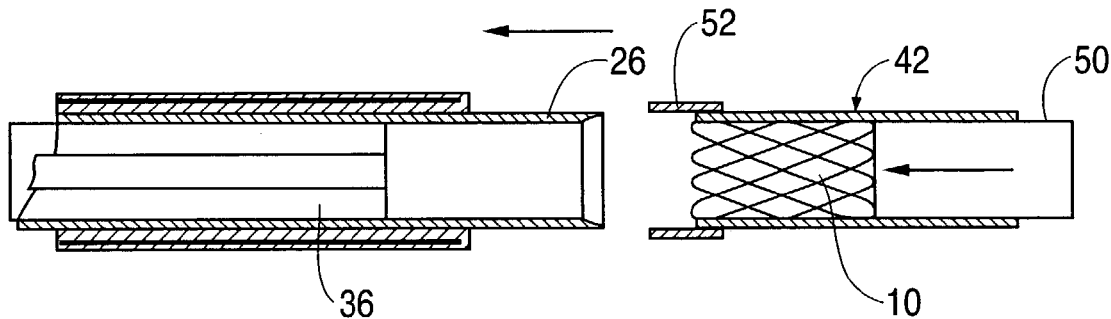
FIG. 5A is a cross-sectional view of the loading apparatus with the woven tube at the end of the loading apparatus and the nose assembly removed from the delivery device.
Figure 5B:
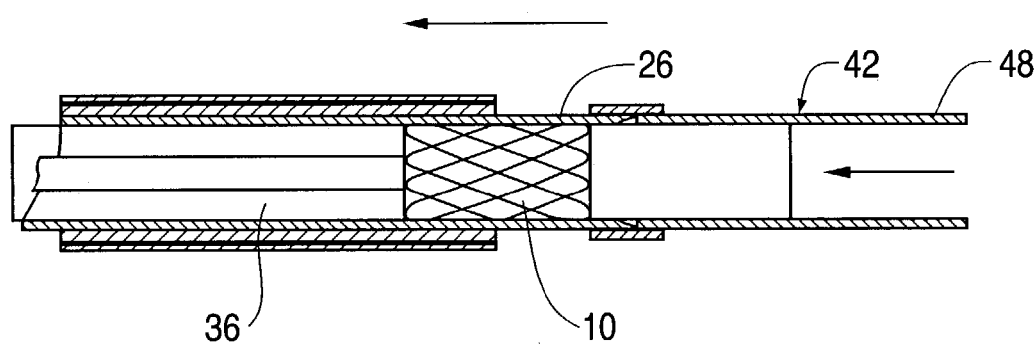
FIG. 5B shows the loading apparatus in place on the end of the protective sleeve. Movement of the plunger in the loading apparatus positions the woven tube inside the protective sleeve.
Figure 5C:
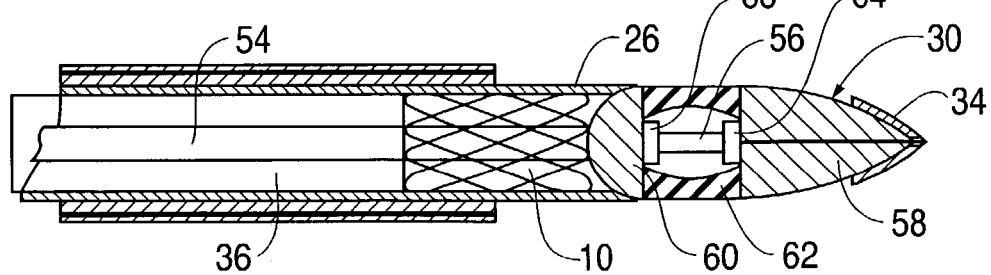
FIG. 5C shows the woven tube loaded inside the protective sleeve of the delivery device with the nose assembly in place.

With reference to the sequences of FIGS. 4D, 4E, 4F, 4G and 4H, the nose assembly 30 is moved away from the proximal end of the protective sleeve 26 as shown in FIG. 4D. Simultaneously, the cylindrical ram 36 and the alignment sleeve 40 are advanced toward the proximal end of the protective sleeve 26 also as shown in FIG. 4D. The cylindrical ram 36 partially forces the woven tube 10 out of the end of the protective sleeve 26 while the alignment sleeve 40 compresses the two layers of intestine 28, 32.

The woven tube 10 is continued to be deployed by further advancing the cylindrical ram 36 toward the proximal end of the protective sleeve 26 as shown in FIG. E. At the same time, the alignment sleeve 40 is advanced to the proximal end of the protective sleeve 26 and pushes the tissues from the protective sleeve 26 toward the center of the woven tube 10 before full deployment of the woven tube.

As shown in FIG. F, the woven tube 10 is forced out of the protective sleeve 26 by moving the cylindrical ram 36 to the proximal end of the protective sleeve 26. At the same time, alignment struts 44 housed in grooves in the alignment sleeve 40 are moved into a predetermined angular position to support the intestinal walls 28, 30. The alignment struts 44 may be, for example, spring wire or nitinol wire in its superelastic phase.

FIG. G shows the woven tube 10 fully deployed. At this stage, the alignment struts 44 are still positioned to support the intestinal walls 28, 30.

As shown in FIG. H, the alignment struts 44 have been retracted into their housing in the alignment sleeve 40. The streamlined nose 58 has been moved toward the distal end of the deliver device 22 by means of the second hollow shaft 56. This movement causes a compression of the hollow rubber or plastic cylinder 62 which forms a compressed buttress 62' in abutting contact with the deployed woven tube 10 to ensure complete closure.

In order to remove the device from the deployed woven tube 10, the hollow rubber or plastic cylinder 62 is retracted into nose assembly 30 by movement of the second hollow shaft 56. The delivery device 22 is then removed from the center of the deployed woven tube 10 as shown in FIG. 4I.

FIG. 4J shows an alternative embodiment in which the alignment struts 44 have been replaced with an alignment buttress mechanism 46. FIG. 4J shows the same delivery sequence as FIG. 4F. As shown in FIG. 4J, the proximal end of the alignment buttress mechanism 46 is attached to the proximal end of the alignment sleeve 40. Thus, deployment of the alignment buttress mechanism 46 causes it to assume a looped configuration insuring proper placement of the tissue during closure of the woven tube 10. The alignment buttress mechanism 46 may be, for example, a plastic mesh sleeve or a plastic tube with longitudinal slits.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. A method of deploying an anastomosis device, comprising mounting a woven tube of wire having a first end and a second end inside a protective sleeve, inserting the device into a body cavity through a trochar or tube to a predetermined puncture site of a first segment either proximal or distal to a desired anastomotic site, advancing the device intraluminally to the anastomotic site either manually or with the aid of a guide wire, bringing a second tissue segment into close apposition to the first segment at the anastomotic site, piercing a wall of the first segment and a wall of the second segment and into a lumen of the second segment, deploying the tube from the protective sleeve at a juncture of apposing puncture holes created by the device, and forming a petal configuration wherein the first end and the second end of the tube form interdigitated petals at the anastomotic site to hold the two segments in apposition.

2. The method of claim 1, wherein the first and second segments are intestinal segments.

3. The method of claim 1, wherein one of the first and second segments is a bile duct and the other of the first and second segments is the jejunum.

4. The method of claim 1, wherein the anastomosis is a side-to-side anastomosis.

5. The method of claim 1, wherein the mechanical force of the woven tube to hold the two segments in apposition is selected such that the deployed tube remains temporarily in place until sufficient healing of the segments occurs at which time the tube sloughs from the segments leaving a properly functioning anastomosis.

6. The method of claim 1, wherein the device is advanced to the anastomotic site with the aid of a previously positioned guide wire.

7. The method of claim 1, wherein the tube is deployed from the protective sleeve by a ram housed in the protective sleeve.

8. The method of claim 1, wherein tissues are pushed from the protective sleeve onto the tube during deployment by an alignment sleeve associated with the protective sleeve.

9. The method of claim 1, wherein the tissues are properly placed during deployment of the tube by an alignment mechanism.

10. The method of claim 1, wherein the closure of the deployed tube is ensured by compression of the tube distal from the protective sleeve.

11. A method of deploying an anastomosis device, comprising mounting a woven tube of wire having a substantially constant diameter between a first end and a second end inside a protective sleeve, inserting the device into a body cavity through a trochar or tube to a predetermined puncture site of a first segment either proximal or distal to a desired anastomotic site, advancing the device intraluminally to the anastomotic site either manually or with the aid of a guide wire, bringing a second tissue segment into close apposition to the first segment at the anastomotic site, piercing a wall of the first segment and a wall of the second segment and into a lumen of the second segment, deploying the tube from the protective sleeve at a juncture of apposing puncture holes created by the device, and forming a petal configuration wherein the first end and the second end of the tube form interdigitated petals at the anastomotic site to hold the two segments in apposition.

* * * * *